United States Patent
Valerino, Sr.

(10) Patent No.: US 9,549,784 B1
(45) Date of Patent: Jan. 24, 2017

(54) SHARPS DISPOSING SYSTEM AND METHOD

(71) Applicant: Fredrick M. Valerino, Sr., Timonium, MD (US)

(72) Inventor: Fredrick M. Valerino, Sr., Timonium, MD (US)

( * ) Notice: Subject to any disclaimer, the term of this patent is extended or adjusted under 35 U.S.C. 154(b) by 0 days.

(21) Appl. No.: 15/157,378

(22) Filed: May 17, 2016

(51) Int. Cl.
- *B65G 51/34* (2006.01)
- *G08B 21/18* (2006.01)
- *B65G 51/02* (2006.01)
- *B65G 53/04* (2006.01)
- *G05B 15/02* (2006.01)

(52) U.S. Cl.
CPC ............. *A61B 50/362* (2016.02); *B65G 51/02* (2013.01); *B65G 53/04* (2013.01); *G05B 15/02* (2013.01); *G08B 21/182* (2013.01)

(58) Field of Classification Search
CPC ......... B65G 43/08; B65G 51/34; B65G 51/36; G06F 19/3462; A61J 2205/60; E04F 17/12
USPC .......... 406/2, 3, 13, 110, 176, 197; 700/225, 700/229, 230
See application file for complete search history.

(56) References Cited

U.S. PATENT DOCUMENTS

| | | | |
|---|---|---|---|
| 2,609,190 A * | 9/1952 | Jackson | A47L 5/38 15/301 |
| 2,679,990 A | 6/1954 | Mathzeit et al. | |
| 3,048,875 A * | 8/1962 | Bottinelli | A47L 5/38 137/391 |
| 3,070,403 A | 12/1962 | Shelton | |
| 3,683,759 A * | 8/1972 | Voss | B29C 31/002 493/231 |
| 3,759,577 A | 9/1973 | Manzer | |
| 3,953,078 A | 4/1976 | Aitken | |
| 4,076,321 A | 2/1978 | Haight et al. | |
| 4,084,770 A | 4/1978 | Warmann | |
| 4,108,498 A | 8/1978 | Bentsen | |
| 4,157,796 A | 6/1979 | Warmann | |
| 4,210,801 A | 7/1980 | Gomez et al. | |
| 4,820,086 A | 4/1989 | Kieronski | |
| 4,995,765 A | 2/1991 | Tokuhiro et al. | |
| 5,083,704 A * | 1/1992 | Rounthwaite | B65F 1/0093 15/314 |
| 5,192,170 A | 3/1993 | Lang | |
| 5,217,328 A | 6/1993 | Lang | |
| 5,234,292 A | 8/1993 | Lang | |
| 5,354,000 A | 10/1994 | Wright et al. | |
| 5,385,105 A | 1/1995 | Withers, Jr. et al. | |

(Continued)

OTHER PUBLICATIONS

EXAIR Corporation, Line Vac, 2014, available at www.exair.com.

*Primary Examiner* — Joseph Dillon, Jr.
(74) *Attorney, Agent, or Firm* — Hanna Bondarik Mosolygo

(57) ABSTRACT

Systems, methods, and modes for automatic disposal of sharps in a medical environment via a pneumatic tube system and without a dedicated carrier from one of a plurality of dispersed sending stations to a secured central location. The system comprises a plurality of sending stations, a receiving stations routably connected to the plurality of sending stations via the pneumatic tubing and comprising a receiving container configured for storing sharps received via multiple deliveries, and a pump configured for creating a pressure differentiation within the pneumatic tubing for transmitting the sharps from one of the sending stations to the receiving station. The receiving container may be replaced by another receiving container when the receiving container is full.

40 Claims, 5 Drawing Sheets

(56) References Cited

U.S. PATENT DOCUMENTS

| | | | |
|---|---|---|---|
| 5,402,938 A | 4/1995 | Sweeney | |
| 5,636,947 A | 6/1997 | Valerino, Sr. et al. | |
| 5,712,789 A | 1/1998 | Radican | |
| 5,805,454 A | 9/1998 | Valerino, Sr. et al. | |
| 5,864,485 A | 1/1999 | Hawthorne et al. | |
| 5,896,297 A | 4/1999 | Valerino, Sr. | |
| 6,048,086 A | 4/2000 | Valerino, Sr. | |
| 6,173,212 B1 | 1/2001 | Valerino, Sr. | |
| 6,202,004 B1 | 3/2001 | Valerino, Sr. | |
| 6,283,909 B1 | 9/2001 | Sharp | |
| 6,477,442 B1 | 11/2002 | Valerino, Sr. | |
| 6,561,691 B1 | 5/2003 | McCann et al. | |
| 6,599,476 B1 | 7/2003 | Watson et al. | |
| 6,637,587 B2 | 10/2003 | Britton | |
| 6,702,150 B2 | 3/2004 | Sumetzberger | |
| 6,712,561 B1 | 3/2004 | Valerino, Sr. et al. | |
| 7,241,081 B1* | 7/2007 | Keller | B65G 51/06 406/186 |
| 7,243,002 B1 | 7/2007 | Hoganson et al. | |
| 7,260,447 B2* | 8/2007 | Osborne | B01F 11/0005 700/216 |
| 7,328,084 B1 | 2/2008 | Hoganson et al. | |
| 7,363,106 B1 | 4/2008 | Hoganson et al. | |
| 7,424,340 B2 | 9/2008 | Owens | |
| 7,751,930 B2* | 7/2010 | Valerino, Sr. | B65G 51/06 406/2 |
| 7,824,613 B2* | 11/2010 | Richter | G01N 35/1095 198/346.2 |
| 7,874,768 B1* | 1/2011 | Keller | B65G 51/06 406/188 |
| 8,113,349 B2 | 2/2012 | Sansoucy et al. | |
| 8,116,906 B2 | 2/2012 | Valerino, Sr. | |
| 8,153,001 B2 | 4/2012 | Peters | |
| 8,268,179 B2 | 9/2012 | Peters | |
| 8,371,773 B2 | 2/2013 | Bryan, Jr. et al. | |
| 9,139,383 B2* | 9/2015 | Hoganson | B65G 51/36 |
| 9,352,914 B2* | 5/2016 | Le | B65G 51/32 |
| 2004/0057801 A1* | 3/2004 | Valerino, Sr. | B09B 3/0075 406/197 |
| 2005/0049746 A1 | 3/2005 | Rosenblum | |
| 2015/0025675 A1 | 1/2015 | Valerino, Sr. | |

\* cited by examiner

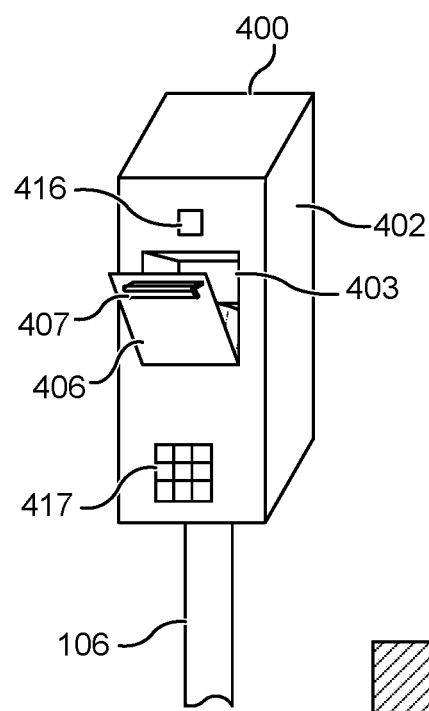
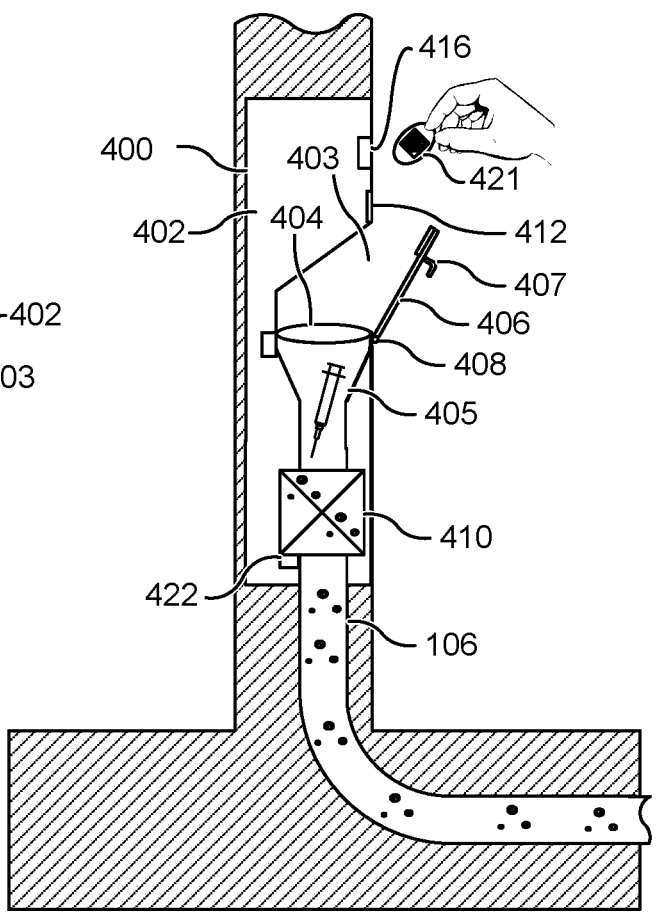
FIG. 4A
FIG. 4B

SHARPS DISPOSING SYSTEM AND METHOD

BACKGROUND OF THE INVENTION

Technical Field

Aspects of the embodiments relate to safe disposal of sharps, and more specifically to systems, methods, and modes for automatic disposal of sharps to a secured central location via pneumatic tubing.

Background Art

Sharps waste is classified as biomedical and biohazardous waste that consist of used objects or devices that were implemented in medical care or in medical or industrial research to puncture or lacerate the skin. Sharps can be made of metal, glass, or plastic and contain sharp or rigid points, corners, edges, or protrusions that can pierce, cut, slice, or scrape the skin. Examples of sharps waste include needles, syringes with and without needles, hypodermic and tubing, acupuncture needles, suture needles, tubing with needles, scalpel blades, blood vials, exposed ends of dental wires, broken glass or capillary tubes, culture dishes and slides, lancets, pipettes, root canal files, trauma scene waste that can cut, slice or pierce, or the like. Sharps are used to treat diabetes, arthritis, cancer, and other diseases, or to obtain blood samples for research to identify diseases.

Unfortunately, used sharps are very dangerous to humans and pets as they can cause accidental needle sticks, cuts, and punctures that can cause serious health conditions, spread infections, and transmit blood-borne diseases. The most common infections include hepatitis B (HBV), hepatitis C (HCV), and Human Immunodeficiency Virus (HIV). Consequently, used sharps must be carefully handled and immediately disposed of after use. Proper sharps disposal also helps protecting the environment.

Used sharps are commonly disposed using dedicated sharps disposal containers dispersed throughout the hospitals in rooms where sharps are utilized, such as patient rooms, emergency rooms (ER), operating rooms (OR), and phlebotomy rooms. These containers are generally made of puncture-resistant plastic and leak-resistant bottom, sides, and lid. Routinely the containers are scheduled for pick up on the floors and placed in a contaminated area at a predesignated contaminated floor enclosure. Then the containers are routinely placed in a contaminated area near the loading dock or an area near an incinerator, in a few instances. Containers picked up by a waste management company are generally brought to a predetermined U.S. Government approved location, where they are emptied, decontaminated, and returned for reuse. If the sharps are emptied into an incinerator, the emptied containers are decontaminated and reused.

From the moment sharps waste is produced, it must be handled as little as possible to reduce risk of injury. Yet, the aforementioned disposal methods require prolonged handling of sharps until they can be properly disposed. The sharps have to be placed in containers, the containers must be collected by personnel from each hospital location and transported to the designated area. Moreover, the containers are accessible to unauthorized personnel, including patients and children. They may also get overfilled and if not emptied timely may increase the risk of accidental needle-stick injury.

Accordingly, a need has arisen for systems, methods, and modes for automatic and safe disposal of sharps to a secured central location via pneumatic tubing that entails minimal amount of handling.

SUMMARY OF THE INVENTION

It is an object of the embodiments to substantially solve at least the problems and/or disadvantages discussed above, and to provide at least one or more of the advantages described below.

It is therefore a general aspect of the embodiments to provide systems, methods, and modes for automatic and safe disposal of sharps to a secured central location via pneumatic tubing that entails minimal amount of handling.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

Further features and advantages of the aspects of the embodiments, as well as the structure and operation of the various embodiments, are described in detail below with reference to the accompanying drawings. It is noted that the aspects of the embodiments are not limited to the specific embodiments described herein. Such embodiments are presented herein for illustrative purposes only. Additional embodiments will be apparent to persons skilled in the relevant art(s) based on the teachings contained herein.

DISCLOSURE OF INVENTION

According to an embodiment, a pneumatic tube system is provided for disposal of sharps in a medical environment without a dedicated carrier. The system comprises a plurality of sending stations each comprising a housing having a first opening on its front face for receiving sharps and a second opening in communication with pneumatic tubing for transporting the sharps from the sending station. The system also comprises a receiving stations routably connected to the plurality of sending stations via the pneumatic tubing, wherein the receiving station comprises a receiving container configured for storing sharps received via multiple deliveries. The system further comprises a pump configured for creating a pressure differentiation within the pneumatic tubing for transmitting the sharps from one of the sending stations to the receiving station. The system is a one-way system configured for allowing the sharps to travel in one direction from one of the sending stations to the receiving station. The various pneumatic tubing pathways from the plurality of sending stations may be merged via one or more Y-connectors. In another embodiment, the system may comprise a diverter comprising a plurality of inlet ports each in communication with a selected sending station via pneumatic tubing, wherein the diverter is controlled by a system controller to receive the sharps from an inlet port in communication with a receiving station from which the sharps are transported.

According to an embodiment, the second opening of each sending station comprises a funnel portion that tapers from a wide end to a narrow end, wherein the wide end is in communication with the first opening and wherein the narrow end is in communication with a terminal end of the pneumatic tubing, wherein the funnel portion is configured for guiding the sharps into the pneumatic tubing. The first opening or the second opening may comprise a door to restrict access to the sending station. The second opening may comprise a valve configured for releasing pressure created by the pump such that the user can maintain the door opened. The sending station may comprise a door open sensor configured for sensing that the door has been opened, wherein the door open sensor is configured for triggering activation of the pump. The sending station may comprise a proximity or motion sensor configured for detecting the proximity of a user to trigger at least one of opening of the door and activation of the pump. The door may comprise a lock and the sending station may comprise a user interface for receiving user identification information to authenticate the user and unlock the door upon successful authentication.

According to an embodiment, the sending station may comprise a grinder configured for grinding the sharps before they are transmitted through the pneumatic tubing. The sending station may comprise a proximity or motion sensor in proximity to the grinder configured for sensing sharps in proximity of the grinder and triggering activation of the grinder. The first opening or the second opening of the sending station may comprise a door that includes a door open sensor configured for sensing that the door has been opened and triggering activation of the grinder.

According to an embodiment, the receiving container of the receiving station may comprise an opening configured for mating with a terminal end of pneumatic tubing. The receiving station may comprise a connector configured for releasably attaching the terminal end of the pneumatic tubing to the opening of the receiving container. The receiving container may comprises a sealing cap configured for sealing the opening when the receiving container is being replaced.

According to an embodiment, the receiving station may comprise a fill-level sensor configured for sensing whether the receiving container is full and triggering an indicator to indicate that the receiving container is full. The receiving container may comprise a door that may be opened to empty the receiving container.

According to an embodiment, the pneumatic tubing comprises a flexible reinforced hose that is resistant to needle puncture. The hose may comprise a smooth inner surface to prevent the sharps from being caught in the hose. The hose may comprises a material, including but not limited to plastic, polyvinyl chloride (PVC), polyethylene, polypropylene, rubber, silicone, metal, aluminum alloy, corrugated stainless steel alloy, reinforced or coated fabric, including polyester, nylon, or fiberglass, and any combinations thereof. The hose may comprise an inner diameter ranging from approximately one inch to approximately three inches in size.

According to an embodiment, the pump may create one of a positive pressure or a negative pressure within the pneumatic tubing. The pump may create pressure ranging from approximately four pounds to approximately six pounds of pressure. According to one embodiment, the system may comprise a plurality of pumps each located in proximity to a respective sending station and comprises a positive pressure air compressor. The second opening of the sending station may connected to a substantially vertical portion of pneumatic tubing that is connected to a substantially horizontal portion of pneumatic tubing via a bend; wherein the pump is connected at the bend in a T configuration and aligned with the horizontal portion of pneumatic tubing, wherein the sharps are dropped via gravity along the vertical portion until reaching the bend and then travel along the horizontal portion via a positive pressure created by the pump. According to another embodiment, the pump may comprise an in-line pump connected to a compressed air source configured for creating a positive pressure at an outlet of the in-line pump. According to yet another embodiment, the pump may be located in proximity to the receiving station and may comprise a negative pressure air compressor.

According to an embodiment, the system may further comprise a system controller in signal communication with the plurality of sending stations and the receiving station, wherein the system controller is configured for capturing tracking information associated with sending and receiving the sharps, wherein at least one of the sending station and receiving station comprises an identifying tag reader configured for reading an ID tag attached to the sharps. The identifying tag reader may be configured to read tags, including but not limited to an optically scannable identifier tag, a barcode, a radio-frequency identification (RFID) tag, a near field communication (NFC) tag, or any combinations thereof. The tracking information may comprise at least one of an ID of the sending station, an ID of the sending user, information obtained from the ID tag, a time and date the sharps were sent by the sending station, a time and date the sharps were received by the receiving station, and any combinations thereof.

According to another embodiment, a method is provided of disposing of sharps in a medical environment via a pneumatic tube system and without a dedicated carrier from one of a plurality of dispersed sending stations to a receiving station located in a secure area. The method comprises: (i) receiving sharps via a first opening on a front face of a sending station of the plurality of sending stations routably connected to the receiving station via pneumatic tubing and transporting the sharps from the sending station through a second opening in communication with pneumatic tubing; (ii) creating a pressure differentiation via a pump within the pneumatic tubing for transmitting the sharps from the sending station to the receiving station; (iii) receiving the sharps at a receiving station comprising a receiving container configured for storing sharps received via multiple deliveries; and (vi) replacing the receiving container by another receiving container when the receiving container is full.

BRIEF DESCRIPTION OF THE DRAWINGS

The above and other objects and features of the embodiments will become apparent and more readily appreciated from the following description of the embodiments with reference to the following figures. Different aspects of the embodiments are illustrated in reference figures of the drawings. It is intended that the embodiments and figures disclosed herein are to be considered to be illustrative rather than limiting. The components in the drawings are not necessarily drawn to scale, emphasis instead being placed upon clearly illustrating the principles of the aspects of the embodiments. In the drawings, like reference numerals designate corresponding parts throughout the several views.

BRIEF DESCRIPTION OF THE SEVERAL VIEWS OF THE DRAWING

Figure 1:
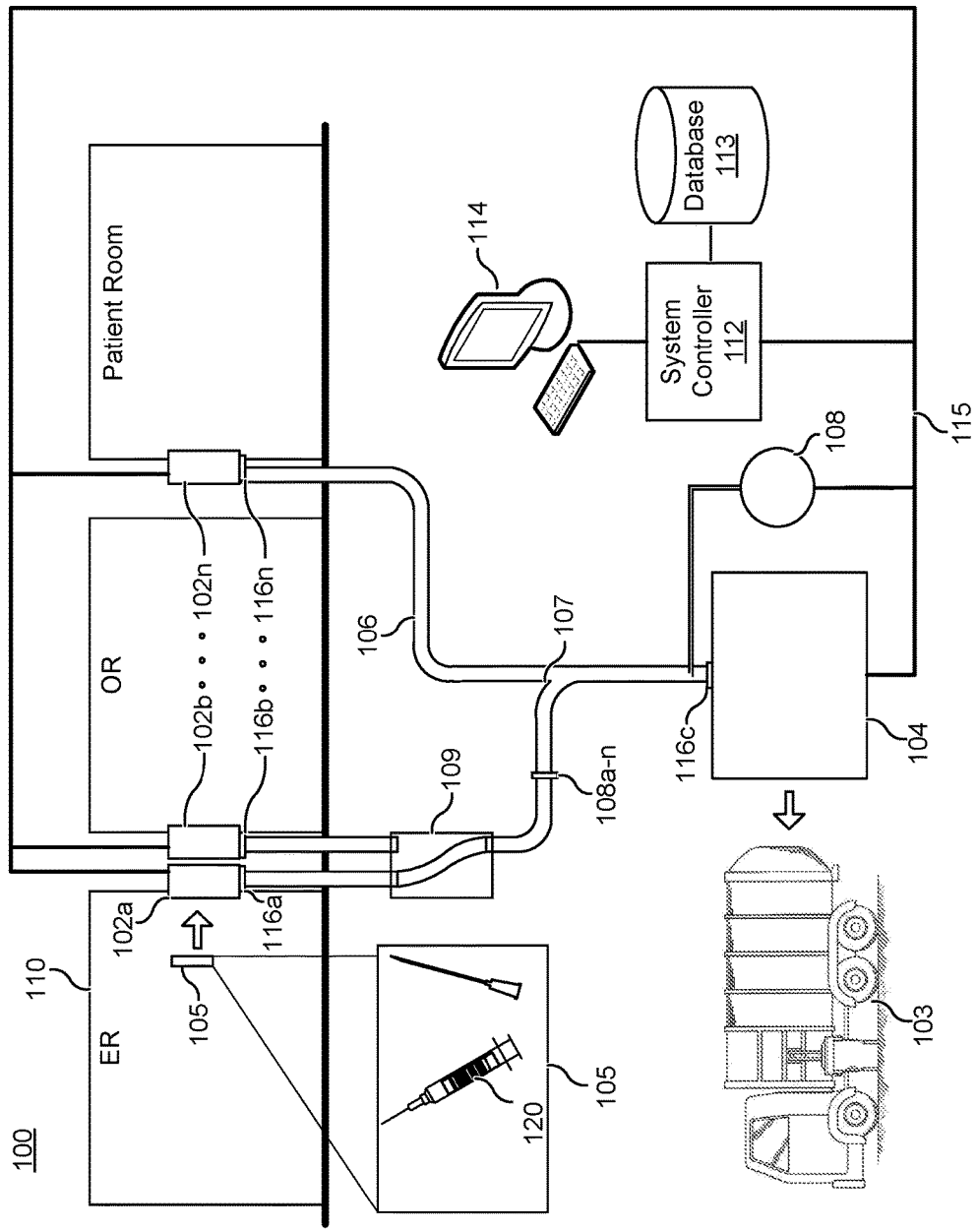
Figure 2A:
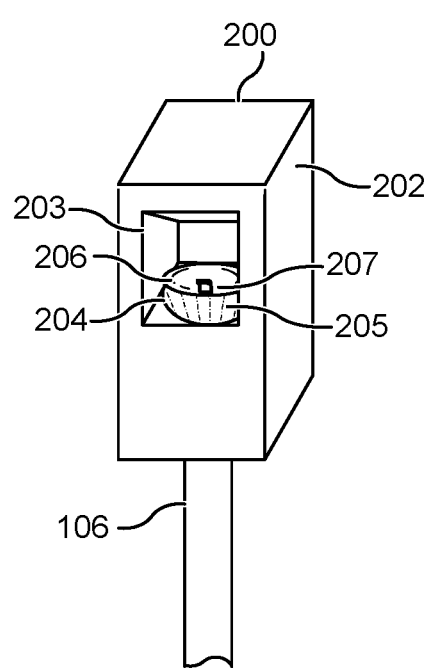
Figure 2B:
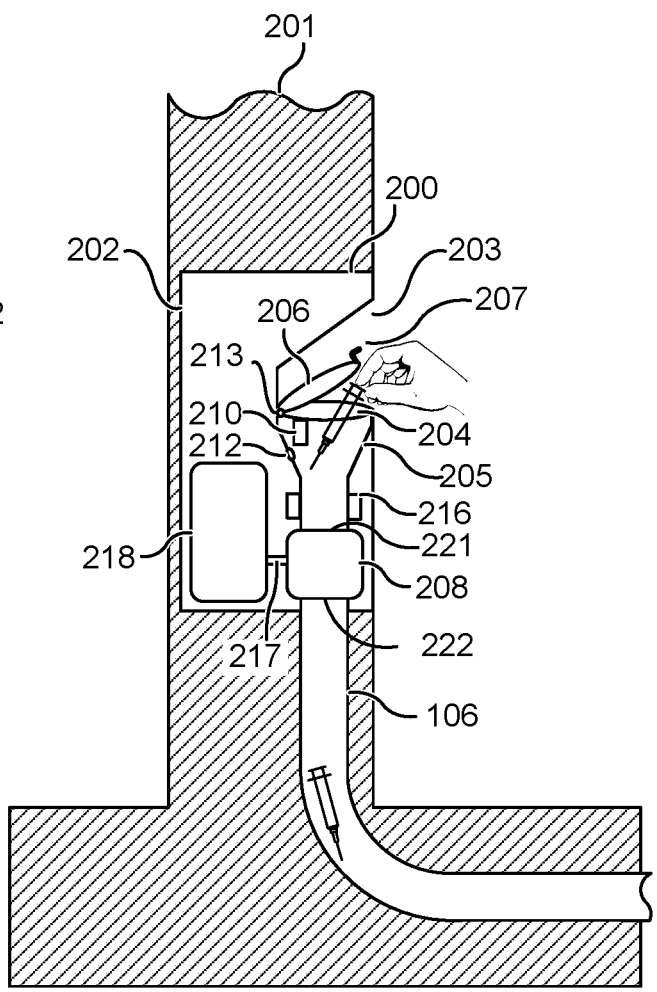
Figure 3A:
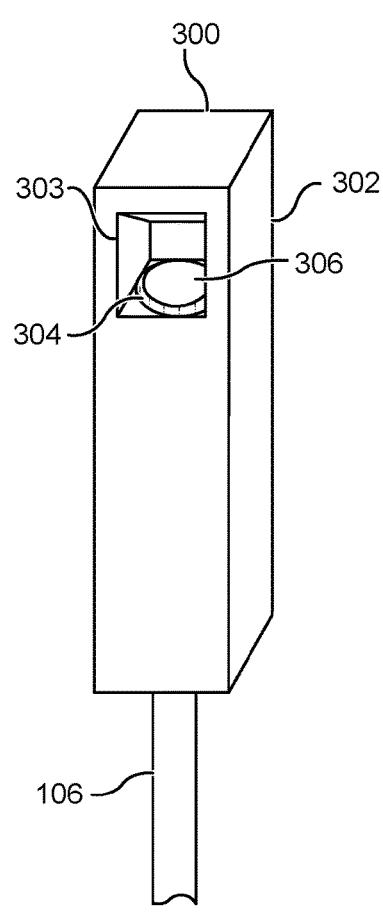
Figure 3B:
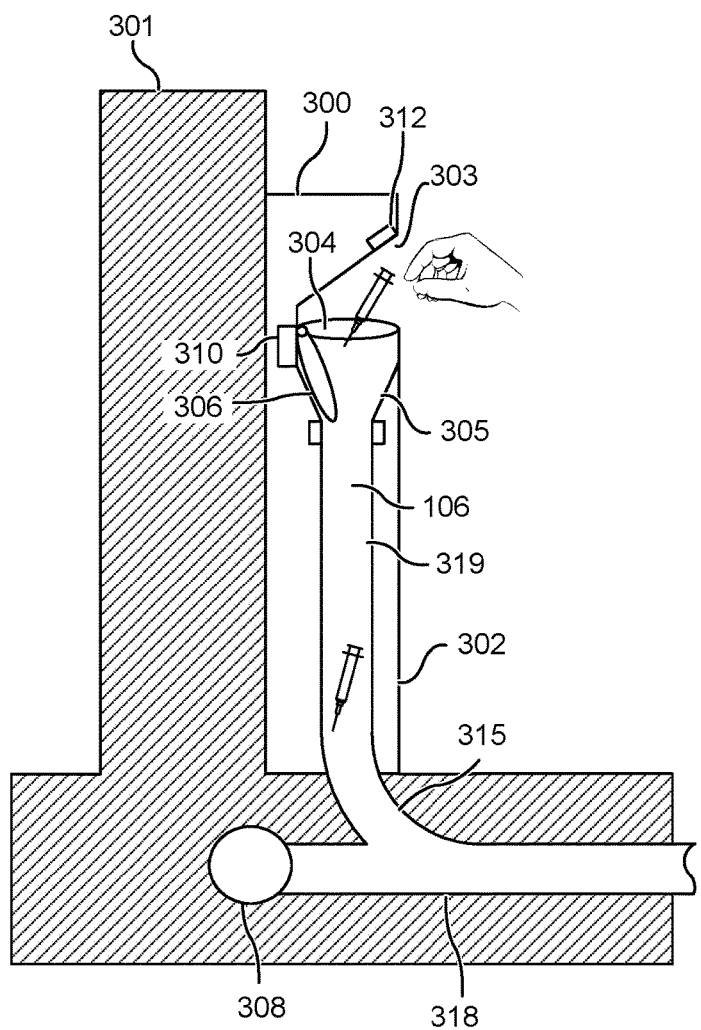
Figure 5:
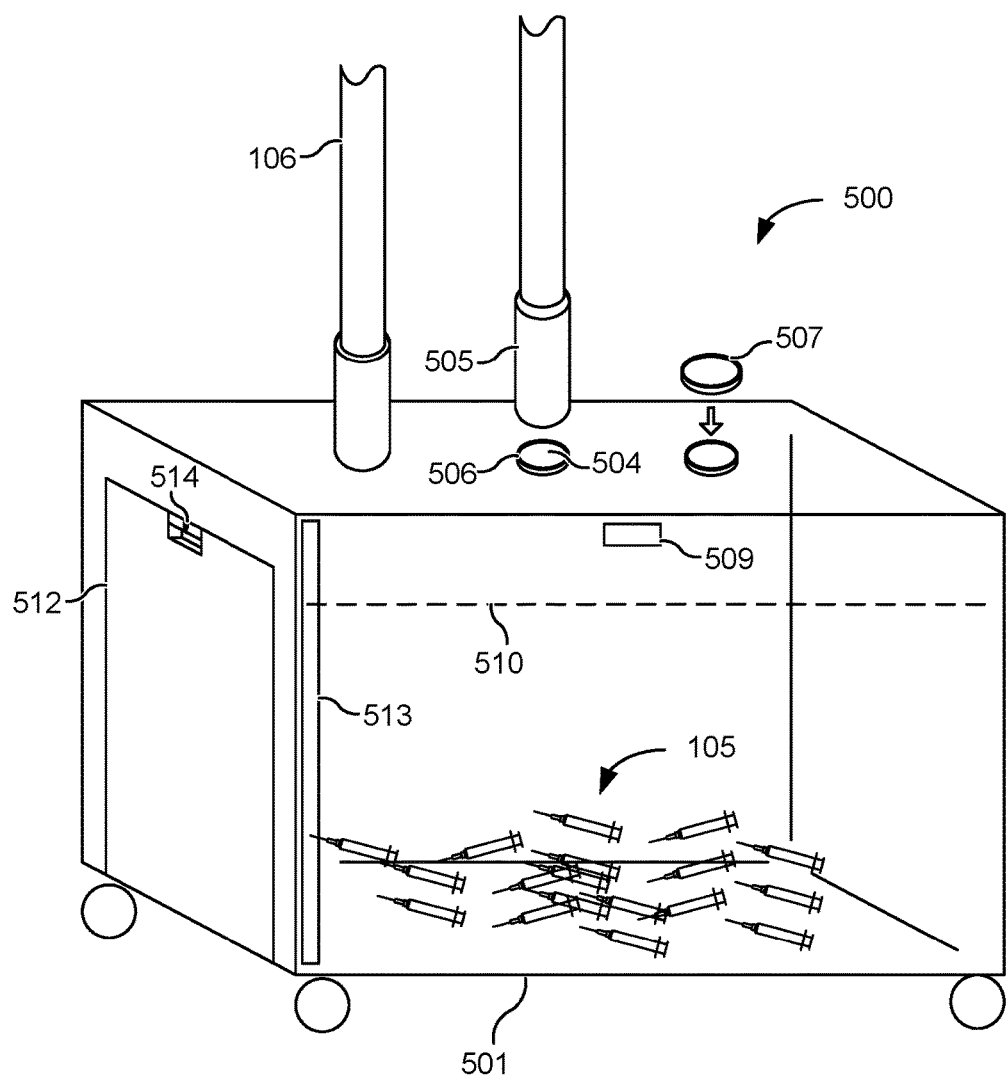

FIG. 1 illustrates a block diagram of a pneumatic system for disposing sharps according to an illustrative embodiment;

FIG. 2A illustrates a perspective view of a pneumatic sending station according to an illustrative embodiment;

FIG. 2B illustrates a partially cross-sectional side view of the pneumatic sending station in FIG. 2A according to an illustrative embodiment;

FIG. 3A illustrates a perspective view of a pneumatic sending station according to another illustrative embodiment;

FIG. 3B illustrates a partially cross-sectional side view of the pneumatic sending station in FIG. 3A according to an illustrative embodiment;

FIG. 4A illustrates a perspective view of a pneumatic sending station according to another illustrative embodiment;

FIG. 4B illustrates a partially cross-sectional side view of the pneumatic sending station in FIG. 4A according to an illustrative embodiment; and FIG. 5 illustrates a perspective view of a receiving station according to an illustrative embodiment.

DETAILED DESCRIPTION OF THE INVENTION

The embodiments are described more fully hereinafter with reference to the accompanying drawings, in which embodiments of the inventive concept are shown. In the drawings, the size and relative sizes of layers and regions may be exaggerated for clarity. Like numbers refer to like elements throughout. The embodiments may, however, be embodied in many different forms and should not be construed as limited to the embodiments set forth herein. Rather, these embodiments are provided so that this disclosure will be thorough and complete, and will fully convey the scope of the inventive concept to those skilled in the art. The scope of the embodiments is therefore defined by the appended claims.

Reference throughout the specification to "one embodiment" or "an embodiment" means that a particular feature, structure, or characteristic described in connection with an embodiment is included in at least one embodiment of the embodiments. Thus, the appearance of the phrases "in one embodiment" on "in an embodiment" in various places throughout the specification is not necessarily referring to the same embodiment. Further, the particular feature, structures, or characteristics may be combined in any suitable manner in one or more embodiments.

The different aspects of the embodiments described herein pertain to the context of systems, methods, and modes for disposal of sharps, but is not limited thereto, except as may be set forth expressly in the appended claims. While the present principles are described with respect to sharps disposed at a hospital, the present principles may also be used in, but are not limited to, other medical or industrial facilities, physician offices, managed care facilities, nursing homes, long term care, rest areas, pharmacies, blood test centers, laboratories, such as clinical laboratories, biotechnology or pharmaceutical manufacturers' facilities, or other facilities where sharps disposal is generated.

Aspects of the embodiments relate to systems, methods, and modes for automatic and safe disposal of sharps to a secured central location via pneumatic tubing. Referring to FIG. 1, there is shown a diagram illustrating a pneumatic system 100 for disposing sharps according to an embodiment of the present principles. System 100 is configured for receiving and transporting any type of medical sharps, including but not limited to needles, syringes with and without needles, hypodermic and tubing, acupuncture needles, suture needles, tubing with needles, scalpel blades, blood vials, exposed ends of dental wires, broken glass or capillary tubes, culture dishes and slides, lancets, pipettes, root canal files, trauma scene waste that can cut, slice or pierce, or the like.

System 100 comprises one or more sending stations 102a-n connected to a receiving station 104 via pneumatic tubing 106. Each sending station 102a-n is configured for receiving sharps 105 and automatically transporting the sharps 105 via pneumatic tubing 106 to the receiving station 104. Each sending station 102a-n may be configured for receiving a plurality of sharps simultaneously for simultaneous transport. Sending stations 102a-n may be strategically installed in locations throughout a building, such as a hospital, where conventional sharps disposal containers are currently located. For example, sending stations 102a-n may be installed in various locations 110, including patient rooms, emergency rooms (ER), operating rooms (OR), phlebotomy rooms, nurses' stations, pharmacies, intensive care units (ICU), or other locations that routinely generate sharps waste.

The receiving station 104 may be located in a secure area within the hospital designated as a contaminated area. According to an embodiment, the receiving station 104 may be located in proximity to a waste disposal area, such as a loading dock. The receiving station 104 may comprise a large receiving container, as later shown and described, capable of receiving vast amount of sharps 105 via multiple deliveries. After getting filled, the receiving container of the receiving station 104 may be sealed and picked up by a waste management company 103 and replaced by another receiving container. The receiving container may be transported by the waste management company 103 to a predetermined U.S. government approved location to be emptied. In another embodiment, the hospital may comprise an incinerator. The sharps 105 arriving at the receiving station 104 may be periodically disposed in the incinerator and destroyed.

According to aspects of the present embodiment, system 100 operates without the implementation of any dedicated pneumatic carriers. Instead, sharps 105 are directly transported within the pneumatic tubing 106. Accordingly, immediately after the sharps 105 are used in a procedure, the user may dispose of the sharps 105 directly via one of the sending stations 102a-n. The sharps 105 are then quickly transported to the receiving station 104. Since the sharps 105 are immediately disposed of without the use of any containers or carriers, there is no danger that the container or the carrier may get overfilled. Moreover, no individual carriers or containers need to get loaded at the sending stations 102a-n or emptied every time the receiving station 104 receives a delivery of sharps 105. Accordingly, system 100 speeds up the disposal process and effectively reduces the extent a user handles the sharps, significantly reducing the risk of accidental needle-stick injury.

According to some aspects of the embodiments, pneumatic tubing 106 may comprise a flexible reinforced hose that is resistant to needle puncture. Such a hose may comprise flexible plastic material, such as polyvinyl chloride (PVC), polyethylene, polypropylene, or the like. Although, other materials may also be utilized, including rubber; reinforced or coated fabric, such as polyester, nylon, fiberglass, or the like; silicone; metals such as aluminum alloy, corrugated stainless steel alloy, or the like; or other material known in the art. The hose may comprise a smooth inner surface to prevent the sharps 105 from being caught in the hose. The inner diameter of the hose may range from approximately 1 inch to approximately 3 inches. According to an embodiment, the inner diameter may comprise approximately 1⅝ inches or 1½ inches. Accordingly, the hose is large enough to permit the transport of sharps 105 such as needles, while maintaining small enough inner diameter to reduce the amount of air pressure or vacuum required to efficiently transport the sharps 105 therein. Moreover, the present pneumatic system 100 can be easily installed throughout a hospital due to the flexibility and compact size of the pneumatic tubing 106.

According to some aspects of the embodiments, system 100 may comprise a point-to-point pneumatic system. According to another embodiment, system 100 may comprise a multi-station pneumatic system 100, as shown in FIG. 1, comprising a plurality of sending stations 102a-n connected to a receiving station 104 via a plurality of tubing pathways. Although FIG. 1 demonstrates a one zone pneumatic tube system 100, a system with multiple zones and the inclusion of any number of sending stations 102a-n and receiving stations 104 is possible without deviating from the scope of the present principles. The various pneumatic tubing pathways may be combined or merged via one or more Y-connectors 107. According to another embodiment, system 100 may comprise one or more diverters 109 configured for changing the direction of the tubing pathways. For example, diverter 109 may comprise an inner flexible tube that can travel via rails or robotic arms to align with one of a plurality of incoming ports to receive sharps 105 from either sending station 102a or sending station 102b.

According to an embodiment, system 100 is a one-way system such that sharps 105 may only travel from the sending stations 102a-n to the receiving station 104 in one direction, and not backward. This ensures safety of transmissions and prevents system misuse. System 100 comprises a pump 108 configured for creating pressure differentiation within the pneumatic tubing 106 that facilitates the transmission of sharps 105 from the sending stations 102a-n to the receiving station 104. Depending on pump location with respect to the receiving station 104, pump 108 may either create a positive pressure or a negative pressure within pneumatic tubing 106 to move sharps 105 within the tubing 106. According to an embodiment, pump 108 is configured for generating approximately 4 pounds to approximately 6 pounds of pressure/vacuum. According to one embodiment, pump 108 may comprise a positive pressure air compressor for generating compressed air within pneumatic tubing 106. In such an implementation, for example, each sending station 102a-n may comprise a positive pressure air compressor for generating compressed air within pneumatic tubing 106 in proximity to each sending station 102a-n (as shown in FIG. 3B). Such positive pressure air compressor 108 may be configured to provide positive air pressure to push sharps 105 from one of the sending stations 102a-n to the receiving station 104. Alternatively, according to an embodiment the pump 108 may comprise a negative pressure compressor or a vacuum pump 108 that creates vacuum within pneumatic tubing 106. In such an implementation, for example, the receiving station 104 may comprise a vacuum pump 108 (as shown in FIG. 1) that pulls the sharps 105 from the sending stations 102a-n to the receiving station 104 with negative air pressure.

System 100 may further comprise a system controller 112 configured for monitoring and controlling the operation of system 100. The one or more sending stations 102a-n, the receiving station 104, the diverter 109, the pump 108, and other system components, may be connected via a wired or wireless signal communication network 115 with, and controlled by, the system controller 112. Although a single system controller 112 is illustrated, a plurality of system controllers may be utilized. For example, each sending station 102a-n may comprise a satellite controlling unit. According to another embodiment, the system controller 112 may be integrated within the receiving station 104.

In one embodiment, the system controller 112 may comprise at least one central processing unit (CPU). The CPU can represent one or more microprocessors, "general purpose" microprocessors, special purpose microprocessors, application specific integrated circuits (ASICs), or any combination thereof. The CPU can provide processing capability to execute an operating system, run various applications, and/or provide processing for one or more of the techniques and functions described herein. Applications that can run on the system controller 112 can include, for example, software for configuring and operating the pneumatic tube system 100. The system controller 112 may further include a memory communicably coupled to the CPU, which can store data and executable code. The memory can represent any suitable storage medium, such as volatile and/or non-volatile memory, including random-access memory (RAM), read-only memory (ROM), Flash memory, hard disk drive, or the like. In buffering or caching data related to operations of the CPU, the memory can store data associated with applications running on the system controller 112.

The system controller 112 can further comprise one or more interfaces, such as a communication network interface, an analog interface, a wireless network interface, or the like, for connecting to communication network 115. According to an embodiment, the network interface may comprise an Ethernet interface for sending and receiving signals over an Internet Protocol (IP) based network. According to one embodiment, the communication network 115 can provide a wired connection between system components. According to another embodiment, the communication network 115 can comprise a wireless network, such as an IEEE 802.11 based network or Wi-Fi.

Each sending station 102a-n, and/or receiving station 104 can comprise a memory and a CPU, such as a microcontroller-based PC board, configured for communicating with and processing various commands and performing operations requested by the system controller 112. Each sending station 102a-n and receiving station 104 can further comprise a network interface configured for bidirectional communication on the communication network 115 with the system controller 112. The network interface can comprise an analog interface, a communication network interface, a wireless interface, such as a radiofrequency transceiver, or the like.

System controller 112 may communicate with a database 113 for logging various data. The database 113 may be, for example, a relational database, a flat file database, fixed length record database, or any other data storage mechanism known or as yet undiscovered in the art. Further, the database 113 may reside on a stand-alone server, or the same machine as the system controller 112. The system controller 112 may interpret the data in the database 113 and generate commands in the form of signals to individual components in system 100 to control the actions of the system 100. The system controller 112 may control various components of the system 100, such as the pump 108 or diverter 109, via relays. In another embodiment, the various components of the system 100, such as sending station 102a-n and receiving station 104, may comprise microprocessors configured for interpreting commands received from the system controller 112. The system controller 112 may send commands to pump 108 to activate and thereby create pressure differentiation to transport sharps 105 through the pneumatic tubing 106. The system controller 112 may further generate and transmit commands to the diverters 109 to change position and/or direction of the pneumatic tubing path 106 to route the sharps 105 to the receiving station 104 via a particular path in the pneumatic transmission tubing 106. In another embodiment, system controller 112 may restrict access to the one or more sending stations 102a-n and provide access only to authorized users as will be described below.

Each sending stations 102a-n and receiving station 104 may further comprise an identifying tag reader 116a-n. Furthermore, the pneumatic tubing 106 may include a plurality of inline identifying tag readers 118a-n disposed at various locations along the pneumatic tubing 106. Tag readers 116a-n and 118a-n may be configured for tracking or sensing the sharps 105 as they are transported through the system 100. Tag readers 116a-n and 118a-n may comprise optical sensors, radiofrequency (RF) readers, or the like. Sharps 105 may comprise identification (ID) tags 120 attached or printed on the sharps 105, for example on a label. ID tags 120 may include, but are not limited to optically scannable identifier tag, radio-frequency identification (RFID) tags, near field communication (NFC) tags, barcodes, or similar ID tags that are capable of being read, sensed, or identified by the tag readers 116a-n and 118a-n. Additionally, any other identification technology known, or as yet undiscovered, may be used within the scope of the present principles. Each ID tag 120 may comprise a unique ID number associated with the sharps 105. The tag readers 116a-n at each sending stations 102a-n and receiving station 104 are configured for reading the ID tags 120 attached to the sharps 105 upon departure and arrival, respectively. Optical inline identifying tag readers 118a-n may be implemented for example, through a window in a section of the tubing 106, through an optical sensor disposed in the tubing 106, or the like. Radiofrequency type identifying tag readers 118a-n may be implemented through a radiofrequency antenna disposed on a recess section of the tubing 106. The inline identifying tag readers 118a-n read, or otherwise sense, the passage of sharps 105 comprising an ID tag 120 that is being transported through the pneumatic tube system 100.

In one embodiment of the present principles, each tag reader 116a-n and 118a-n may be used to record information associated with the ID tags 120 attached to the sharps 105 at various locations throughout the pneumatic tube system 100 and send the recorded information to the system controller 112. According to another embodiment, the system 100 may utilize handheld devices, such as smartphones or personal digital assistants (PDA) (not shown), for reading the ID tags 120 and transmitting recorded information to the system controller 112. The recorded information may include the ID number read from the ID tags 120 associated with the sharps 105. The recorded information may also be appended with other information, such as, but not limited to, date and time, location, a unique ID associated with the sending station 102a-n and receiving station 104, a unique ID associated with the user sending the sharps 105, or other information associated with the transmittal of the sharps 105. The one or more of the appended information may be appended by the tag readers 116a-n and 118a-n, the sending station 102a-n, the receiving station 104, or the system controller 112.

The system controller 112 may receive the recorded information from the tag readers 116a-n at the sending 102a-n and receiving 104 stations, as well as from the inline identifying tag readers 118a-n disposed throughout the pneumatic tube system 100. The system controller 112 may log the recorded information into the database 113. Using the recorded information, the system controller 112 may track each sharp's location throughout the pneumatic tube system 100—as they are sent from the sending stations 102a-n, as they move past inline identifying tag readers 118a-n in the pneumatic tubing 106, and as they are received at the receiving station 104. This creates an auditable trail indicating a chain of custody. The system controller 112 may generate records to show that sharps 105 have been dispatched via sending station 102a-n, received at a receiving station 104, or passed an inline identifying tag reader 118a-n at a certain time. Location recordation may be used to troubleshoot and initiate error notifications, such as a stuck or lost sharps 105. Additionally, reports on chain of custody of sharps 105 may be generated to keep record of who has disposed a specific sharp 105, at which sending station 102a-n, and at which specific point in time.

According to an embodiment, the information stored and recorded by the system controller 112 may be made accessible to users via a computer 114 in communication with the system controller 112 and/or via a web browser with a remote communication device, such as a desktop computer, a laptop computer, or a handheld electronic device, such as a smartphone. In alternative embodiments, this information may be accessible via stand-alone applications, hard copy documents, or any other useful report format. A user may access the information stored and recorded by the system controller 112 to audit compliance with delivery procedures, to generate compliance reporting and manifest system documentation, to track any missing or problem deliveries, to identify or receiving notifications of system errors, such as when sharps get stuck in pneumatic tubing 106, to manage access rights to the pneumatic system to authorized users, among other tasks.

Referring to FIGS. 2A-2B, there is shown an exemplary embodiment of a pneumatic sending station 200, such as sending station 102a-n, where FIG. 2A illustrates a perspective view of the sending station 200 and FIG. 2B illustrates a partially cross-sectional side view of the sending station 200. The pneumatic sending station 200 is utilized in the pneumatic tube system 100 as an interface to the pneumatic tubing 106 to transport sharps 105 to a pneumatic receiving station 104. The sending station 200 may be in signal communication with, and controlled by, the system controller 112 (shown in FIG. 1). The sending station 200 may comprise a housing 202 recessed in a wall 201 within an ER, OR, a patient room, or another location. However, the housing 202 of the sending station 200 may be secured on a wall or to the floor, secured to a counter, attached to a pedestal, or installed via other means within a location. The front face of the housing 202 may include an opening 203 in communication with an opening 204 through a bottom surface of the housing 202 connected to pneumatic tubing 106. The opening 204 may comprise a tapered or funnel portion 205 that is wide at the top end and narrow at the bottom end for guiding the sharps 105 into the pneumatic tubing 106. The bottom end of the funnel portion 205 may correspond to the diameter of the pneumatic tubing 106. For example, the top end of the funnel portion 205 may comprise about 2 inches or about 1¾ inches in diameter that will taper down to a bottom end of about 1⅝ inches in diameter. According to an embodiment, sending station 200 may be configured for receiving a plurality of sharps simultaneously for simultaneous transport.

The opening 204 may further comprise a door 206 configured for closing the top end of the funnel portion 205 to restrict access to the pneumatic tubing 106 so that foreign objects cannot accidentally enter the pneumatic tubing 106. The door 206 may comprise a spring loaded hinge 213 that forces the door 206 shut. The door 206 may comprise a handle 207 that may be pulled by the user to open the door 206. When the handle 207 is released, the spring loaded hinge 213 will force the door 206 to close.

According to an embodiment, sending station 200 may comprise an in-line pump 208. Accordingly, each sensing station 200 in system 100 may comprise an in-line pump 208. Pump 208 may comprise an intake 221 in communication with the funnel portion 205 and an outtake 222 connected to pneumatic tubing 106. The in-line pump 208 may be connected to an air compressor source 218 via an inlet 217 configured for providing compressed air. The in-line pump 208 may be configured for creating a positive pressure at the outtake 222 to transport sharps 105 via pneumatic tubing 106 in one direction from the sending station 200 to the receiving station 104. This in turn creates a negative pressure at the intake 221 that sucks sharps 105 from the opening 204 toward pump 208. The funnel portion 205 at the sending station 200 may comprise a valve or small opening 212 configured for releasing pressure created by the pump 208 inside the funnel portion 205 such that the user can maintain the door 206 opened.

According to another embodiment, system 100 may contain a pump 108 located in the proximity of the receiving station 104 that create negative pressure or vacuum for drawing sharps 105 from the sending station 200 to the receiving station 104.

The sending station 200 may further comprise a door open sensor 210 configured for sensing that the door 206 has been opened. According to an embodiment, door open sensor 210 may be a magnetic contact sensor, a proximity sensor, a mechanical limit switch, or the like. The door open sensor 210 may be configured to trigger the pump 208 to activate or turn on. According to an embodiment, the door open sensor 210 may trigger the sending station 200 to send a signal directly to the pump 208 directing the pump 208 to turn on. In another embodiment, the door open sensor 210 may trigger the sending station 200 to send a "door open" signal to the system controller 112 indicating that the door 206 has been opened at the sending station 200. The system controller 112 may then activate the pump 208 (or pump 108 at the receiving station 104) via a power transistor and/or relay to route the sharps 105 from the sending station 200 to the receiving station 104. Additionally, the system controller 112 may direct any system diverters 109 to create a path to transport the sharps 105 from the sending station 200 from which the system controller 112 received the "door open" signal to the receiving station 104.

According to an embodiment, the system controller 112 may comprise a timer configured for being activated in response to a sensor trigger, such as door open sensor 210 or other sensors described below (e.g., proximity or motion sensor 312). The timer may activate the pump 208 to turn on for a predetermined amount of time sufficient to ensure that contents are delivered to the receiving station 104. According to another embodiment, the pump 208 is activated until the receiving station (e.g., receiving station 500 discussed below) indicates to the system controller 112 that the contents have been received by the receiving station, for example in response to a proximity or motion sensor trigger at the receiving station 500.

According to an embodiment, the sending station 200 may further comprise an identifying tag reader 216 for reading an ID tag 120 attached to a sharp 105. The identifying tag reader 216 may be located in proximity to the narrow bottom end of the funnel portion 205 as shown in FIG. 2B. However, the identifying tag reader 216 can be located in a different location at the sending station 200, for example on a front surface of housing 202 as shown in FIGS. 4A-4B.

In operation, the user may open the door 206 using handle 207. This will cause the door open sensor 210 to trigger, which in turn will cause the pump 208 to activate. The user can then drop the sharps 105 into the opening 204. The sharps 105 are directed using the funnel portion 205 into the pneumatic tubing 106 and substantially immediately transported to the receiving station 104 via the pressure differentiation created within the pneumatic tubing 106.

Furthermore, in a system using identifying tag readers, the identifying tag reader 216 may sense, scan, or otherwise read the ID tag 120 attached to the sharp 105 and transmit recorded information to the system controller 112. According to an embodiment, the recorded information may comprise a unique ID number associated with the sharps 105 as well as other information described above. The system controller 112 may log that information in the database 113 for tracking purposes.

Referring to FIGS. 3A-3B, there is shown another exemplary embodiment of a pneumatic sending station 300, such as sending station 102a-n, where FIG. 3A illustrates a perspective view of the sending station 300 and FIG. 3B illustrates a partially cross-sectional side view of the sending station 300. In this exemplary embodiment, the sending station 300 is shown to comprise a housing 302 mounted to the wall 301. The front face of the housing 302 may include an opening 303 in communication with an opening 304 within the housing 302 connected to pneumatic tubing 106. The opening 304 may comprise a tapered or funnel portion 305, such as funnel portion 205, for guiding the sharps 105 into the pneumatic tubing 106.

In the embodiment shown in FIGS. 3A-3B, the pneumatic sending station 300 comprises a door 306 configured for closing the opening 304. Unlike in FIGS. 2A-2B, the door 306 may open by descending toward the funnel portion 305. The sending station 300 may further comprise a proximity or motion sensor 312 configured for detecting the proximity of a user. Proximity or motion sensor 312 may comprise a passive infrared (PIR) sensor, a microwave sensor, an ultrasonic sensor, a photoelectric sensor, or the like, or any combinations thereof. The door 306 may comprise an automatic door opener 310 configured for automatically opening the door 306. The automatic door opener 310 may comprise an electric motor, a linear actuator, a rotary actuator, an electrical actuator, a pneumatic actuator, a hydraulic actuator, a combustion powered actuator, a mechanical actuator, or a combination thereof.

System 100 may further comprise a plurality of pumps 308 in proximity to each sending station 300. The sending station 300 may comprise a substantially vertical portion 319 of pneumatic tubing 106 that extends substantially vertically from the funnel portion 305 to a bend 315. The bend 315 may change the direction of the pneumatic tubing 106 from the vertical portion 319 to a horizontal portion 318 of pneumatic tubing 106. The pump 308 may be connected to the pneumatic tubing 106 at the bend 315 in a T configuration and be aligned with the horizontal portion 318. The pump 308 may be a positive pressure air pump, such as a positive displacement air compressor, that directs positive pressure into the horizontal portion 318. Accordingly, when the sharps 105 are received at the funnel portion 305 they are dropped via gravity along the vertical portion 319 towards the bend 315. At the bend 315 the sharps 105 are picked up by the positive pressure to travel along the horizontal portion 318. The horizontal portion 318 may be connected via pneumatic tubing 106 to the receiving station 104.

In operation, the user may place his hand holding the sharps 105 in proximity to the proximity or motion sensor 312. Upon detecting proximity or motion of the user, the sensor 312 may trigger the automatic door opener 310 to open the door 306 and the pump 308 to turn on for a predetermined period of time. The user can then drop the sharps 105 into the opening 304, which are directed using the funnel portion 305 into the pneumatic tubing 106. The sharps 105 are dropped via gravity toward the bend 315 and then substantially immediately transported using positive pressure created by the pump 308 to the receiving station 104.

In yet another embodiment, the funnel portion 305 of the sending station 300 may comprise a proximity or motion sensor configured for detecting the passage of a sharps 105 through the funnel portion 305 and in response to activate the pump 308.

FIGS. 4A-4B illustrate another exemplary embodiment of a pneumatic sending station 400, such as sending station 102a-n, where FIG. 4A illustrates a perspective view of the sending station 400 and FIG. 4B illustrates a partially cross-sectional side view of the sending station 400. Sending station 400 may comprise a housing 402 including at its front face an opening 403 in communication with an opening 404 within the housing 402 connected to pneumatic tubing 106. The opening 404 may comprise a tapered or funnel portion 405 for guiding the sharps 105 into the pneumatic tubing 106.

The pneumatic sending station 400 may further comprise a door 406 configured for closing the opening 403 on the front face of the housing 402 to restrict access to the pneumatic tubing 106. The door 406 may comprise a spring loaded hinge 408 that forces the door 406 shut. The door 406 may comprise a handle 407 that may be pulled by the user to open the door 406. The door 406 may also comprise a lock 412, such as an electromagnetic lock, that keeps the door 406 closed in place. Other types of locks may also be utilized, such as a key lock.

The front face of the sending station 400 may further comprise a user interface 417 including a keypad for receiving user input. In another embodiment, the user interface 417 may include a touch-screen to receive inputs directly from a user touching the touch-screen. The user interface 417 may be utilized to enter security information (e.g., a personal identification number (PIN)) for a user of the sending station 400. The sending station 400 may communicate with the system controller 112 to verify whether the entered PIN belongs to an authorized user. The system controller 112 may query a list of authorized users stored on the database 113 to authenticate a user. Upon successful user authentication, the lock 412 of the door 406 may be released to allow the user to open the door 406 via door handle 407 to access opening 404 to dispose sharps 105. When the handle 407 is subsequently released, the spring loaded hinge 408 will force the door 406 to close. A successful user authentication, and thereby door unlock, may also trigger the system controller 112 to activate or turn on the pump 108 for a predetermined amount of time, and direct any diverters, to route the sharps 105 from the sending station 400 to the receiving station 104.

In operation, the user may enter the user's ID using the user interface 417. The sending station 400 may communicate the entered user's ID to the system controller 112 for authentication. Upon successful authentication, the system controller 112 may unlock the lock 412 of door 406 and turn on the pump 108. Then user can open the door 406 using handle 407, and drop the sharps 105 into the opening 404. The sharps 105 are directed using the funnel portion 405 into the pneumatic tubing 106 and substantially immediately transported to the receiving station 104.

According to another embodiment, the front face of the sending station 400 may further comprise an identifying tag reader 416, such as an identifying tag reader 116a-n discussed above. The sending user may scan the ID tag 120 attached to the sharps 105 with the identifying tag reader 416 log tracking data, as discussed above. Additionally, an ID tag 421 may be associated with a sending user. The sending users ID tag 421 may be a key fob, a card, a badge, a wristband, or the like. The user ID tag 421 may contain security information, such as a user's personal identification number, for a user of sending station 400. The sending user may scan the sending user ID tag 421, the identifying tag reader 416 may read the user's personal identification number, and the sending station 400 may communicate with the system controller 112 to verify whether the personal identification number belongs to an authorized user. The system controller 112 may query a list of authorized users stored on the database 113 to authenticate a user. Upon successful user authentication, the lock 412 of the door 406 may be released to allow the user to open the door 406 via door handle 407 to access opening 404 to dispose sharps 105. When the handle 407 is subsequently released, the spring loaded hinge 408 will force the door 406 to close. A successful user authentication, and thereby door unlock, may also trigger the system controller 112 to activate or turn on the pump 108 for a predetermined amount of time, and direct any diverters 109, to route the sharps 105 from the sending station 400 to the receiving station 104.

In another embodiment, a more passive system may be used for scanning the ID tag 120 attached to the sharps 105 and the user ID tag 421. The identifier tags may be RFID tags which can be read by an RFID identifying tag reader. In such an embodiment, the sending user at the sending station 400 may move near the RFID identifying tag reader 416 while holding the sharps 105, and the reader will read and send the ID information from the sending user and the sharps to the system controller 112. Thus, sending users may advantageously avoid physically scanning each identifier tag. The scanned information from the sending station 400 is transmitted to the system controller 112 where it is stored in the database 113 and interpreted by the system controller 112.

According to another embodiment, sending station 400 may further comprise a crusher, pulverizer, or grinder 410. The grinder 410 may be used for grinding sharps 105 that are being disposed at the sending station 400. The grinder 410 may comprise an electric motor and grinding blades or rings. The grinder 410 may be located proximate to the narrow or bottom end of the funnel portion 405. The grinder 410 may be located away from the opening 404 at a distance preventing possible contact by the user. When the sharps are disposed into opening 404, the funnel portion 405 guides the sharps 105 into the grinder 410 to be crushed before entering the pneumatic tubing 106. The grinder 410 ensures that the sharps are easily transported through the pneumatic tubing 106. Grinding the sharps 105 also provides for additional storage space at the receiving station 104. The grinder 410 may be activated by the system controller 112 upon successful user authentication after the user scans the user ID tag 421.

According to another embodiment, sending station 400 may comprise a proximity or motion sensor 422 in proximity to the grinder 410 configured for sensing sharps 105 in proximity of the grinder 410. When sharps 105 are disposed in opening 404, are guided by funnel portion 405, and come in proximity of the grinder 410, the proximity or motion sensor 422 gets triggered. A trigger of the proximity or motion sensor 422 may cause to activate a timer and turn the power of the grinder 410 on for a predetermined amount of time.

Although each sending station 200, 300, and 400 discussed above is shown with one or more particular types of components, a sending station may include any combination of the components discussed above. For example, grinder 410 may be included in the sending station 200 (shown in FIGS. 2A-2B) and be activated in response to the trigger of the door open sensor 210. In yet another embodiment, grinder 410 may be included in the sending station 300 (shown in FIGS. 3A-3B) and be activated in response to the trigger of the proximity or motion sensor 312. Also, the pump configuration shown in FIG. 3B may be applied to sending stations 200 or 400. Alternatively, sending stations 300 and 400 may each comprise an in-line pump 208. In sending station 400, the in-line pump 208 may be located before or after the pulverizer 410.

FIG. 5 illustrates an embodiment of the receiving station 500, such as receiving station 104. Receiving station 500 may be located in a secure area within the hospital designated as a contaminated area. The receiving station 500 may be located in proximity to a waste disposal area, such as a loading dock. The receiving station 500 may comprise a large receiving container 501 capable of receiving vast amount of sharps 105 via multiple deliveries. The receiving station 500 is utilized in the pneumatic tube system 100 as an interface to the pneumatic tubing 106 to receive sharps 105 from one or more sending stations 102a-n. The receiving station 500 may be in signal communication with, and controlled by, the system controller 112 (shown in FIG. 1). The receiving container 501 may comprise one or more openings 504 configured for mating with a terminal end of pneumatic tubing 106. A plurality of openings 504 may be included for receiving a plurality of incoming pneumatic tubing 106 connected to a plurality of sending stations 102a-n. According to an embodiment, the pneumatic tubing 106 may comprise a connector 505 and each opening 504 may comprise a lip 506. The connector 505 may be configured for mating with or attaching to the lip 506, for example through threading, magnetic contact, screws, bolt, pipe fitting, clamp, friction fitting, or the like. As such, pneumatic tubing 106 may be tightly secured to the opening 504 to prevent access to sharps 105 therein.

The receiving station 500 may comprise a fill-level sensor 509 configured for sensing whether the receiving container 501 is full. The fill-level sensor 509 may comprise an ultrasonic wireless level sensor. The fill-level sensor 509 may communicate with the system controller 112 to issue an alarm when the fill-level sensor 509 senses that the waste at the receiving container 501 have reached a predetermined threshold level 510. In another embodiment, the outer surface of the receiving container 501 may comprise a light indicator, such as a red light emitting diode (LED), to indicate that the receiving container 501 is full. Thus, although the receiving container 501 may be replaced periodically, the fill-level sensor 509 may indicate if it is full before a scheduled replacement. In yet another embodiment, the receiving container 501 may comprise a see through window 513 configured for enabling a user to see the fill level of the container.

After getting filled, the connector 505 of the pneumatic tubing 106 may be disconnected from the receiving container 501, and the openings 504 in the receiving container 501 may be sealed using sealing caps 507. The receiving container 501 of the receiving station 500 may be picked up by a waste management company 103 and replaced by another receiving container 501. The receiving container may be transported by the waste management company 103 to a predetermined U.S. government approved location for burial. In another embodiment, the hospital may comprise an incinerator. The sharps 105 arriving at the receiving station 500 may be periodically disposed in the incinerator and destroyed. The receiving container may comprise a door 512 that may be opened to empty the receiving container 501. The door 512 may be secured with a lock 514, such as an electromagnetic lock.

INDUSTRIAL APPLICABILITY

The disclosed embodiments provide a system, software, and a method for automatic and safe disposal of sharps. It should be understood that this description is not intended to limit the embodiments. On the contrary, the embodiments are intended to cover alternatives, modifications, and equivalents, which are included in the spirit and scope of the embodiments as defined by the appended claims. Further, in the detailed description of the embodiments, numerous specific details are set forth to provide a comprehensive understanding of the claimed embodiments. However, one skilled in the art would understand that various embodiments may be practiced without such specific details.

Although the features and elements of aspects of the embodiments are described being in particular combinations, each feature or element can be used alone, without the other features and elements of the embodiments, or in various combinations with or without other features and elements disclosed herein.

This written description uses examples of the subject matter disclosed to enable any person skilled in the art to practice the same, including making and using any devices or systems and performing any incorporated methods. The patentable scope of the subject matter is defined by the claims, and may include other examples that occur to those skilled in the art. Such other examples are intended to be within the scope of the claims.

The above-described embodiments are intended to be illustrative in all respects, rather than restrictive, of the embodiments. Thus the embodiments are capable of many variations in detailed implementation that can be derived from the description contained herein by a person skilled in the art. No element, act, or instruction used in the description of the present application should be construed as critical or essential to the embodiments unless explicitly described as such. Also, as used herein, the article "a" is intended to include one or more items.

All United States patents and applications, foreign patents, and publications discussed above are hereby incorporated herein by reference in their entireties.

Alternate Embodiments

Alternate embodiments may be devised without departing from the spirit or the scope of the different aspects of the embodiments.

What is claimed is:

1. A pneumatic tube system that disposes sharps in a medical environment without a dedicated carrier, comprising:
 a plurality of sending stations each comprising a housing having a first opening on its front face for receiving sharps and a second opening in communication with pneumatic tubing for transporting the sharps from the sending station;
 a receiving station routably connected to the plurality of sending stations via the pneumatic tubing, wherein the receiving station comprises a receiving container configured for storing sharps received via multiple deliveries; and
 a pump configured for creating a pressure differentiation within the pneumatic tubing for transmitting the sharps from one of the sending stations to the receiving station, wherein the pump comprises an in-line pump connected to a compressed air source configured for creating a positive pressure at an outlet of the in-line pump.

2. The system according to claim 1, wherein the second opening comprises a funnel portion that tapers from a wide end to a narrow end, wherein the wide end is in communication with the first opening and wherein the narrow end is in communication with a terminal end of the pneumatic tubing, wherein the funnel portion is configured for guiding the sharps into the pneumatic tubing.

3. The system according to claim 1, wherein the first opening or the second opening comprises a door to restrict access to the sending station.

4. The system according to claim 3, wherein the second opening comprises a valve configured for releasing pressure created by the pump such that the user can maintain the door opened.

5. The system according to claim 3, wherein the sending station comprises a door open sensor configured for sensing that the door has been opened, wherein the door open sensor is configured for triggering activation of the pump.

6. The system according to claim 3, wherein the sending station comprises a proximity or motion sensor configured for detecting the proximity of a user to trigger at least one of opening of the door and activation of the pump.

7. The system according to claim 3, wherein the door comprises a lock.

8. The system according to claim 7, wherein the sending station comprises a user interface for receiving user identification information to authenticate the user and unlock the door upon successful authentication.

9. The system according to claim 1, wherein the sending station comprises a grinder configured for grinding the sharps before they are transmitted through the pneumatic tubing.

10. The system according to claim 9, wherein the sending station comprise a proximity or motion sensor in proximity to the grinder configured for sensing sharps in proximity of the grinder and triggering activation of the grinder.

11. The system according to claim 9, wherein the first opening or the second opening comprises a door that comprises a door open sensor configured for sensing that the door has been opened and triggering activation of the grinder.

12. The system according to claim 1, wherein the receiving container of the receiving station comprises an opening configured for mating with a terminal end of pneumatic tubing.

13. The system according to claim 12, wherein the receiving station comprises a connector configured for releasably attaching the terminal end of the pneumatic tubing to the opening of the receiving container.

14. The system according to claim 12, wherein the receiving container comprises a sealing cap configured for sealing the opening when the receiving container is being replaced.

15. The system according to claim 1, wherein the receiving station comprises a fill-level sensor configured for sensing whether the receiving container is full and triggering an indicator to indicate that the receiving container is full.

16. The system according to claim 1, wherein the receiving container comprises a door that may be opened to empty the receiving container.

17. The system according to claim 1, wherein the system is a one-way system configured for allowing the sharps to travel in one direction from one of the sending stations to the receiving station.

18. The system according to claim 1, wherein various pneumatic tubing pathways from the plurality of sending stations are merged via one or more Y-connectors.

19. The system according to claim 1 further comprising a diverter comprising a plurality of inlet ports each in communication with a selected sending station via pneumatic tubing, wherein the diverter is controlled by a system controller to receive the sharps from an inlet port in communication with a receiving station from which the sharps are transported.

20. The system according to claim 1, wherein the pneumatic tubing comprises a flexible reinforced hose that is resistant to needle puncture.

21. The system according to claim 20, wherein the hose comprises a smooth inner surface to prevent the sharps from being caught in the hose.

22. The system according to claim 20, wherein the hose comprises material selected from the group consisting of plastic, polyvinyl chloride (PVC), polyethylene, polypropylene, rubber, silicone, metal, aluminum alloy, corrugated stainless steel alloy, reinforced or coated fabric, including polyester, nylon, or fiberglass, and any combinations thereof.

23. The system according to claim 20, wherein the hose comprises an inner diameter ranging from approximately one inch to approximately three inches in size.

24. The system according to claim 1, wherein the pump creates one of a positive pressure or a negative pressure within the pneumatic tubing.

25. The system according to claim 1, wherein the pump creates pressure ranging from approximately four pounds to approximately six pounds of pressure.

26. The system according to claim 1, comprising a plurality of pumps each located in proximity to a respective sending station and comprises a positive pressure air compressor.

27. The system according to claim 26 wherein the second opening of the sending station is connected to a substantially vertical portion of pneumatic tubing that is connected to a substantially horizontal portion of pneumatic tubing via a bend; wherein the pump is connected at the bend in a T configuration and aligned with the horizontal portion of pneumatic tubing, wherein the sharps are dropped via gravity along the vertical portion until reaching the bend and then travel along the horizontal portion via a positive pressure created by the pump.

28. The system according to claim 1, wherein the pump is located in proximity to the receiving station and comprises a negative pressure air compressor.

29. The system according to claim 1, further comprising a system controller in signal communication with the plurality of sending stations and the receiving station, wherein the system controller is configured for capturing tracking information associated with sending and receiving the sharps, wherein at least one of the sending station and receiving station comprises an identifying tag reader configured for reading an ID tag attached to the sharps.

30. The system according to claim 29, wherein the identifying tag reader is configured to read tags consisting of at least one of an optically scannable identifier tag, a barcode, a radio-frequency identification (RFID) tag, a near field communication (NFC) tag, or any combinations thereof.

31. The system of according to claim 30, wherein tracking information comprises at least one of an ID of the sending station, an ID of the sending user, information obtained from the ID tag, a time and date the sharps were sent by the sending station, a time and date the sharps were received by the receiving station, and any combinations thereof.

32. A method of disposing of sharps in a medical environment via a pneumatic tube system and without a dedicated carrier from one of a plurality of dispersed sending stations to a receiving station located in a secure area, the method comprising:
receiving sharps via a first opening on a front face of a sending station of the plurality of sending stations routably connected to the receiving station via pneumatic tubing and transporting the sharps from the sending station through a second opening in communication with pneumatic tubing;
creating a pressure differentiation via a pump within the pneumatic tubing for transmitting the sharps from the sending station to the receiving station, wherein the pump comprises an in-line pump connected to a compressed air source configured for creating a positive pressure at an outlet of the in-line pump;
receiving the sharps at a receiving station comprising a receiving container configured for storing sharps received via multiple deliveries; and
replacing the receiving container by another receiving container when the receiving container is full.

33. A pneumatic tube system that disposes sharps in a medical environment without a dedicated carrier, comprising:
a plurality of sending stations each comprising a housing having a first opening on its front face for receiving sharps and a second opening in communication with pneumatic tubing for transporting the sharps from the sending station, wherein the second opening comprises a funnel portion that tapers from a wide end to a narrow end, wherein the wide end is in communication with the first opening and wherein the narrow end is in communication with a terminal end of the pneumatic tubing, wherein the funnel portion is configured for guiding the sharps into the pneumatic tubing;
a receiving station routably connected to the plurality of sending stations via the pneumatic tubing, wherein the receiving station comprises a receiving container configured for storing sharps received via multiple deliveries; and
a pump configured for creating a pressure differentiation within the pneumatic tubing for transmitting the sharps from one of the sending stations to the receiving station.

34. A pneumatic tube system that disposes sharps in a medical environment without a dedicated carrier, comprising:
a plurality of sending stations each comprising: a housing having a first opening on its front face for receiving sharps and a second opening in communication with pneumatic tubing for transporting the sharps from the sending station, wherein the first opening or the second opening comprises a door to restrict access to the sending station;
a receiving station routably connected to the plurality of sending stations via the pneumatic tubing, wherein the receiving station comprises a receiving container configured for storing sharps received via multiple deliveries; and
a pump configured for creating a pressure differentiation within the pneumatic tubing for transmitting the sharps from one of the sending stations to the receiving station;
wherein at least one sending station comprises a proximity or motion sensor configured for detecting the proximity of a user to trigger at least one of opening of the door and activation of the pump.

35. A pneumatic tube system that disposes sharps in a medical environment without a dedicated carrier, comprising:
a plurality of sending stations each comprising a housing having a first opening on its front face for receiving sharps and a second opening in communication with pneumatic tubing for transporting the sharps from the sending station;
a receiving station routably connected to the plurality of sending stations via the pneumatic tubing, wherein the receiving station comprises a receiving container configured for storing sharps received via multiple deliveries; and
a pump configured for creating a pressure differentiation within the pneumatic tubing for transmitting the sharps from one of the sending stations to the receiving station;
wherein at least one sending station comprises a grinder configured for grinding the sharps before they are transmitted through the pneumatic tubing.

36. A pneumatic tube system that disposes sharps in a medical environment without a dedicated carrier, comprising:
a plurality of sending stations each comprising a housing having a first opening on its front face for receiving sharps and a second opening in communication with pneumatic tubing for transporting the sharps from the sending station;
a receiving station routably connected to the plurality of sending stations via the pneumatic tubing, wherein the receiving station comprises a receiving container configured for storing sharps received via multiple deliveries, wherein the receiving container of the receiving station comprises an opening configured for mating with a terminal end of pneumatic tubing, wherein the receiving station comprises a connector configured for releasably attaching the terminal end of the pneumatic tubing to the opening of the receiving container; and
a pump configured for creating a pressure differentiation within the pneumatic tubing for transmitting the sharps from one of the sending stations to the receiving station.

37. A pneumatic tube system that disposes sharps in a medical environment without a dedicated carrier, comprising:
a plurality of sending stations each comprising a housing having a first opening on its front face for receiving sharps and a second opening in communication with pneumatic tubing for transporting the sharps from the sending station;

a receiving station routably connected to the plurality of sending stations via the pneumatic tubing, wherein the receiving station comprises a receiving container configured for storing sharps received via multiple deliveries, wherein the receiving container of the receiving station comprises an opening configured for mating with a terminal end of pneumatic tubing, wherein the receiving container comprises a sealing cap configured for sealing the opening when the receiving container is being replaced; and a pump configured for creating a pressure differentiation within the pneumatic tubing for transmitting the sharps from one of the sending stations to the receiving station.

38. A pneumatic tube system that disposes sharps in a medical environment without a dedicated carrier, comprising:

a plurality of sending stations each comprising a housing having a first opening on its front face for receiving sharps and a second opening in communication with pneumatic tubing for transporting the sharps from the sending station;

a receiving station routably connected to the plurality of sending stations via the pneumatic tubing, wherein the receiving station comprises a receiving container configured for storing sharps received via multiple deliveries;

a pump configured for creating a pressure differentiation within the pneumatic tubing for transmitting the sharps from one of the sending stations to the receiving station; and a diverter comprising a plurality of inlet ports each in communication with a selected sending station via pneumatic tubing, wherein the diverter is controlled by a system controller to receive the sharps from an inlet port in communication with a receiving station from which the sharps are transported.

39. A pneumatic tube system that disposes sharps in a medical environment without a dedicated carrier, comprising:

a plurality of sending stations each comprising a housing having a first opening on its front face for receiving sharps and a second opening in communication with pneumatic tubing for transporting the sharps from the sending station;

a receiving station routably connected to the plurality of sending stations via the pneumatic tubing, wherein the receiving station comprises a receiving container configured for storing sharps received via multiple deliveries; and a plurality of pumps each located in proximity to a respective sending station and comprises a positive pressure air compressor, wherein each pump is configured for creating a pressure differentiation within the pneumatic tubing for transmitting the sharps from one of the sending stations to the receiving station.

40. A pneumatic tube system that disposes sharps in a medical environment without a dedicated carrier, comprising:

a plurality of sending stations each comprising a housing having a first opening on its front face for receiving sharps and a second opening in communication with pneumatic tubing for transporting the sharps from the sending station;

a receiving station routably connected to the plurality of sending stations via the pneumatic tubing, wherein the receiving station comprises a receiving container configured for storing sharps received via multiple deliveries;

a pump configured for creating a pressure differentiation within the pneumatic tubing for transmitting the sharps from one of the sending stations to the receiving station; and a system controller in signal communication with the plurality of sending stations and the receiving station, wherein the system controller is configured for capturing tracking information associated with sending and receiving the sharps, wherein at least one of the sending station and receiving station comprises an identifying tag reader configured for reading an ID tag attached to the sharps.

* * * * *